United States Patent
Duncan et al.

(10) Patent No.: US 6,255,338 B1
(45) Date of Patent: Jul. 3, 2001

(54) USE OF CALCIUM INTRACELLULAR STORE INACTIVATORS AND FORMULATIONS THEREOF AS CELL GROWTH INHIBITORS

(75) Inventors: George Duncan, Cringlefors; Michael Wormstone; Peter Davies, both of Norwich; Christopher Liu, Brighton, all of (GB)

(73) Assignees: The University of East Anglia; The Norfolk & Norwich Health Care NHS Trust, both of Norwich (GB)

( * ) Notice: Subject to any disclaimer, the term of this patent is extended or adjusted under 35 U.S.C. 154(b) by 0 days.

(21) Appl. No.: 08/952,355

(22) PCT Filed: May 17, 1996

(86) PCT No.: PCT/GB96/01183

§ 371 Date: Jun. 29, 1998

§ 102(e) Date: Jun. 29, 1998

(87) PCT Pub. No.: WO96/36334

PCT Pub. Date: Nov. 21, 1996

(30) Foreign Application Priority Data

May 20, 1995 (GB) .................................................. 9510238
May 19, 1995 (GB) .................................................. 9510180
Aug. 11, 1995 (GB) .................................................. 9516458

(51) Int. Cl.$^7$ ......................... A61K 31/34; C07D 307/77

(52) U.S. Cl. ............................................. 514/468; 549/299
(58) Field of Search ...................................... 549/299, 514, 549/468

(56) References Cited

U.S. PATENT DOCUMENTS 5,384,128  1/1995  Meezan et al. ....................... 424/450

FOREIGN PATENT DOCUMENTS

WO 94/16648  8/1994  (WO) .
WO 95/10273  4/1995  (WO) .
WO 96/00073  1/1996  (WO) .

OTHER PUBLICATIONS

Griffin, et al., Effects of the Pyrrolizidine Alkaloid Senecionine and the Alkenals trans–404 Hexanal and trans–2–Hexenol, Biochem. Pharm., vol. 38, No. 3 pp. 391–397, 1989.*

(List continued on next page.)

Primary Examiner—Alan L. Rotman
Assistant Examiner—Binta Robinson
(74) Attorney, Agent, or Firm—Synnestvedt & Lechner LLP

(57) ABSTRACT

The use of a calcium intracellular store inactivator for inhibiting cell growth is disclosed; for example, thapsigargin or a derivative may be used to inhibit intraocular lens cell growth. Formulations include an emulsion of the compound for coating an IOL, either ex vivo or in vivo.

18 Claims, 2 Drawing Sheets

OTHER PUBLICATIONS

Figure 1A:
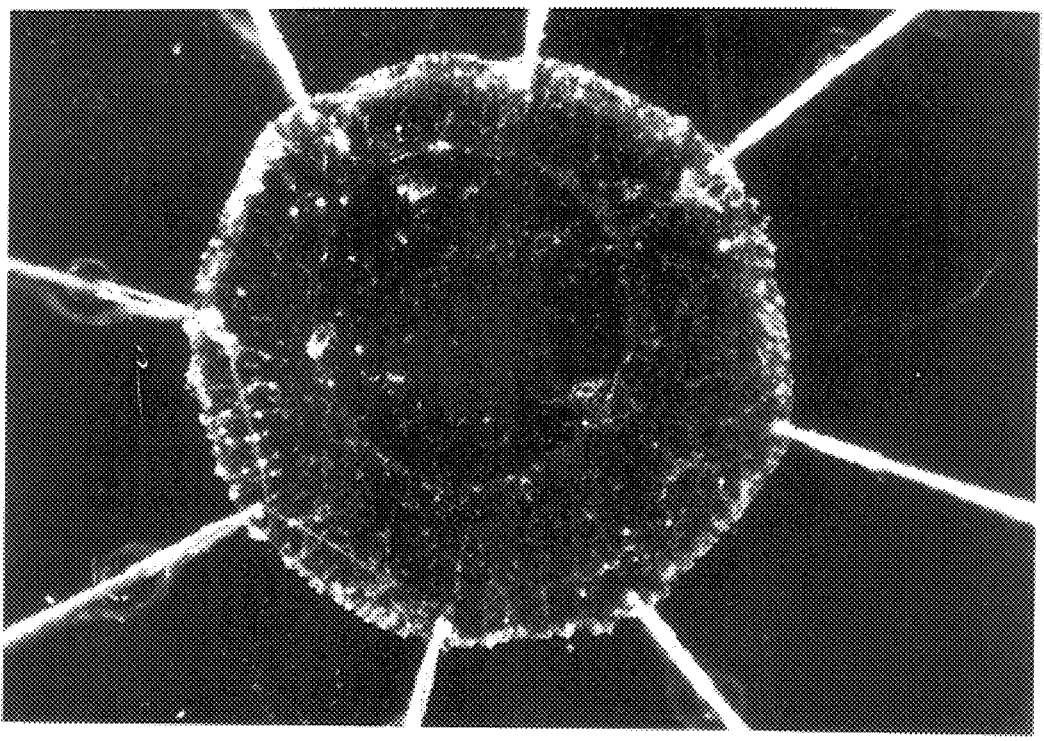

Andersen, et. al., Selective Transformations of the Ca 2+ Pump Inhibitor Thapsigargin, Acta. Chemica Scandinavica 48:340–346, 1994.*

Andersen, et. al., Selective Transformations of the Ca 2+ Pump Inhibitor Thapsigargin, Acta, Chemica Scandinavica 48:340–346, 1994.*

Cohen et al., *JERMOV, Montpellier Meeting, Programme & Abs. Bk.* (1994).

*Technical Note #15, The Messenger,* 3(1) (1994).

Thastrup et al., *Proc. Natl. Acad. Sci, USA,* 87, 2466–70 (1990).

Thastrup et al., *Agents Actions,* 43, 187–93 (1994).

Ghosh et al., *Journal of Biol. Chem.,* 266, 24690–7 (1991) (on order).

Liu et al., *Investigative Ophthalmology & Visual Sci.,* 37(5), 906–14 (1996).

Seidler et al., *J. Biol. Chem.,* 30, 17816–23 (1989) (on order).

Dernouchamps, *Doc. Ophthamol.,* 53, 193–248 (1982) (on order).

Du et al., *J. Physiol. London,* 475P, 33–34P (1994) (on order).

Duncan et al., *Prog. In Retinal & Eye Res.,* 13(2), 623–652 (1994).

Duncan et al., *Cell Calcium,* 19(1), 83–89 (1996).

Delamere & Zudansisky, *Inv. Ophth. & Vis. Sci.,* 36(4), S216 (1995).

Thomas et al, *Investigative Ophthalmology & Visual Science,* 36(4), S589 (1995).

Duncan et al., *Inv. Ophth. & Vis. Sci.* 34(10), 2835–42 (1993).

Christensen et al., *J. Org. Chem.,* 47(4), 649–52 (1982).

*Investigative Ophthalmology & Visual Science,* 37(3), S892 (1996).

*Phytochemistry,* 23(8), 1659–63 (1984).

Graber et al., *J. Biol. Chem.,* 271(2), 883–88 (1996).

Ghosh et al., *Journal of Biol. Chem.,* 266, 24690–7 (1991).

Seidler et al., *J. Biol. Chem.,* 30, 17816–23 (1989).

*Dernouchamps, Doc. Ophthamol.,* 53, 193–248 (1982).

Du et al., *J. Physiol. London,* 475P, 33–34P (1994).

* cited by examiner

USE OF CALCIUM INTRACELLULAR STORE INACTIVATORS AND FORMULATIONS THEREOF AS CELL GROWTH INHIBITORS

CROSS-REFERENCE TO RELATED APPLICATION

This application is a 35 U.S.C. 371 application of PCT/GB96/01183, filed on May 17, 1996.

The present invention relates to the use of calcium intracellular store inactivators such as sesquiterpene lactones, particularly thapsigargin derivatives, and formulations thereof, as cell growth inhibitors, particularly lens cell growth inhibitors. In particular, the invention relates to intraocular lenses coated with such inhibitors.

It is a well-known technique, when a person is suffering from a cataract in the eye, surgically to remove the defective natural lens and implant an artificial lens (intraocular lens or IOL) into the lens capsular bag of the eye. Such artificial lenses are commonly comprised of a plastics material such as polymethyl methacrylate (PMMA) and other acrylic polymers, although silicone-based materials may also be used.

However, one of the well-recognised problems with this technique is that, after a relatively short period of time—a matter of months, perhaps and usually within two to three years—of effecting the lens-replacement operation, a so-called 'after-cataract' may form in the eye. After-cataract is also known as posterior capsular opacification. This after-cataract is caused by lens cells, still present on the anterior capsule of the bag, growing on to the lens posterior capsule (and the anterior surface of the IOL), producing lens proteins and wrinkling of the lens capsule, causing light entering the eye to be scattered.

Various attempts have been made to study the growth of such after-cataracts and of finding ways of preventing or treating such developments. For example, heparin-coated artificial lens has been reported (Cohen et al in JERMOV, Montpellier Meeting, Programme and Abstract Book (1994)) in which FGF (fibroblast growth factor) is attached to heparin and a growth inhibitor attached to the FGF. As the lens cells themselves contain FGF receptors, the heparin-FGF may bind to the lens cells, bringing with it the growth inhibitor which, it is hoped, in turn will kill the lens cells themselves. However, to test whether this system works, there has hitherto been possible only a crude in vitro test which is an attempt to simulate what happens to such an artificial lens in the patient's eye.

In the past, in vivo testing has been done in primates since lower animals do not provide as closely similar an environment to that in humans for the IOL. In lower animals, cells other than lens cells (as well as the lens cells themselves) tend to become involved in the formation of the after-cataract. However, testing on primates is expensive and may still not be fully representative of the human system. Hitherto, the only alternative to such in vivo testing has been in vitro testing by traditional culture methods in which isolated lens cells of the anterior capsule are monitored for growth under usual culture conditions. The present inventors have provided a method for culturing human body cells or tissue suitable for transplanting, which method comprises affixing at discrete points a plurality of such cells to a substrate which itself further comprises a suitable culture medium for the growth of such cells or tissue. For example, it is now possible to culture lens cells by affixing a capsular bag (containing an IOL) at discrete points thereof to a substrate such as a culture dish (for example a Petri dish) which substrate further comprises a suitable culture medium for growth of the lens cells and for representing the natural environment of the capsular bag in the eye.

It has now been found that compounds which inhibit release of the intracellular calcium store (either by "locking" the store in its full or empty states) inhibit or prevent the growth of lens epithelial cells. At least one such compound, a hydrophobic sesquiterpene lactone known generically as 'thapsigargin', is already known. Thapsigargin itself can be extracted from giant hogweed plants or Thapsiagarnica species. Another hydrophobic sesquiterpene lactone, also known (The Messenger 3(1) 1994), is 8-debutanoyl thapsigargin.

Thapsigargin has been described as a tumour-promoter (i.e. which promotes, not inhibits, cell growth) and has been said to affect the calcium ion concentration in intracellular stores so that it produces a histamine response on human skin (Thastrup et al in Proc. Natl. Acad. Sci. USA 87 2466–70 (1990) and Agents Actions 43 187–93 (1994)). Ghosh et al have reported on persistent intracellular calcium pool depletion by thapsigargin and its influence on cell growth (in Journal of Biol. Chem. 266 24690–7 (1991)), but no pharmaceutical composition, delivery device or use has been ascribed to the compound in the context of the eye or cell growth inhibition.

Furthermore, work previously carried out with thapsigargin was undertaken by adding it to a solution of bathing tissue-culture cells. Prior to work carried out by the present inventors, a method did not exist for determining whether or not thapsigargin could inhibit lens cell growth on native cells (i.e. on cells in vivo or ex vivo). Using the method mentioned above, and described in Example 1 hereof and further expounded by Liu et al in Investigative Ophthalmology & Visual Science, 37(5) 906–14 (1996), it was found that not only is thapsigargin effective in inhibiting or preventing the growth of intraocular lens epithelial cells but also that other inhibitors of intracellular calcium store release are effective in so doing.

The present invention now provides a compound suitable for use as a cell growth inhibitor, in particular an intraocular lens epithelial cell growth inhibitor, comprising a calcium intracellular store inactivator, such as either an inhibitor of calcium ATP-ase present in the endoplasmic or sarcoplasmic reticulum which is inert with respect to plasma membrane calcium ATP-ase or an inositol trisphosphate-($IP_3$)-release channel blocker.

Preferably, the compound is lipophilic or hydrophobic and exhibits antimigratory, antiproliferative or cytotoxic characteristics with respect to lens epithelial cells.

Examples of calcium ATP-ase inhibitors are thapsigargin or certain derivatives thereof and cyclopiazonic acid of formula

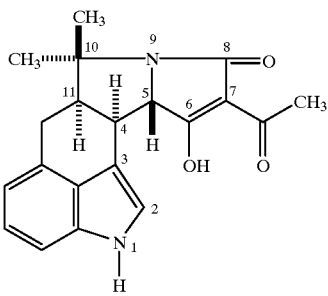

(N. W. Seidler et al J. Biol. Chem. 30 17816–23 (1989)); while examples of $IP_3$-channel blockers include caffeine. The compound preferably comprises thapsigargin or a derivative thereof especially where the 7- and 11-hydroxy groups thereof remain functional. The invention therefore further provides a compound of formula (I):

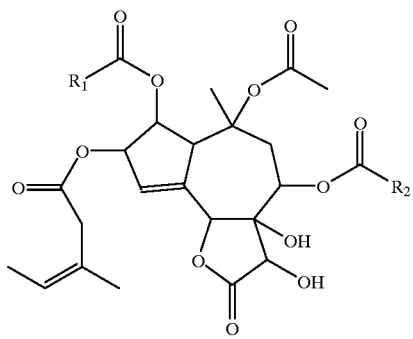

or a salt, ester or prodrug thereof (hereinafter collectively referred to as 'a compound of formula (I)'), other than thapsigargin or 8-debutanoylthapsigargin, as defined hereinabove. Preferably $R_1$ and $R_2$ are straight chain alkyl such as $C_3$ to $C_{10}$ alkyl. More preferably $R_1$ is at least heptyl ($C_7H_{15}$) and $R_2$ is at least propyl ($C_3H_7$).

The present invention therefore further provides a calcium intracellular store inactivator such as a compound of formula (I), including thapsigargin and 8-debutanoylthapsigargin per se, for use as a medicament in the treatment or prevention of cell growth and in particular intraocular lens epithelial cell growth.

However, even once the use of calcium intracellular store inactivators such as thapsigargin, cyclopiazonic acid and caffeine as lens cell growth inhibitors in vivo and ex vivo was invented by the present inventors, there remained the problem of how most appropriately to deliver them to an eye in need of such treatment.

Surprisingly, it has been found that such compounds can be-coated on an IOL which can then be used to deliver calcium intracellular store inactivator into the capsular bag of the eye. The IOL may be coated either ex vivo and then implanted into the eye for slow release of the compound or it may be coated in vivo during the final stages of cataract surgery by means of injecting the calcium intracellular store inactivator behind the IOL in situ. Therefore, an especially preferred aspect of the present invention is the use of the compound, such as a compound of formula (I), for coating an intraocular lens.

Furthermore, the present invention provides a method for preventing or inhibiting cell growth, particularly intraocular lens cell growth, comprising bringing the tissue requiring cell growth inhibition such as the lens capsule into association with a calcium intracellular store inactivator such as a compound of formula (I). Especially preferred is when the tissue is associated with the compound by means of being coated on a tissue implant such as an IOL. Preferably, the method comprises administration to a patient in need thereof of a lens cell growth-inhibiting amount of a calcium intracellular store inactivator such as a compound of formula (I).

It will be clear to the person skilled in the art that the present invention also provides a method for preventing or inhibiting cell growth other than lens cell growth, and therefore that the compounds can be used, for example, as antifouling agents in situations where fungal or other unwanted coverage occurs on surfaces such as ships' hulls and shower enclosures or curtains, and the like. However, in connection with inhibiting lens cell growth, as well as the application of the invention to preventing after-cataract, the compounds are also useful in treating glaucoma patients. For example, in drainage operations to improve the outflow and relieve pressure in the eye of the glaucoma patient, a hole is made near the conjunctiva but this heals over with time due to cell growth. Therefore, application of the compounds, particularly in slow- or sustained-release form, would result in a more successful outcome to the operation.

The compound is therefore preferably administered in the form of a pharmaceutical composition suitable for administration to the eye. Especially preferred is when the composition is in the form of a device such as an intraocular lens.

Therefore, the present invention further provides a pharmaceutical composition comprising a calcium intracellular store inactivator such as a compound of formula (I), including thapsigargin and 8-debutanoylthapsigargin Per se, cyclopiazonic acid or an $IP_3$-channel blocker in association with a pharmaceutically acceptable carrier therefor. Suitable compositions are known to those skilled in the art and include those particularly adapted for intraocular administration such as eye drops, lotions, solid water-soluble polymeric inserts, gels or ointments, or an intraocular lens, or an injection or emulsion suitable for coating thereon.

For example, aqueous or oily suspensions or emulsions may be presented as a dry product for reconstitution with water or other suitable vehicle before use. Such liquid preparations may contain conventional additives such as suspending agents, emulsifying agents, non-aqueous vehicles, preservatives, and if desired conventional colouring agents. For example, a preservative may be included such as those selected from benzalkonium chloride, benzyl alcohol, phenylethyl alcohol, chlorbutol, chlorhexidine or salt thereof such as the acetate, thiomersal, p-hydroxy benzoates, disodium edetate; or a lubricant such as those selected from hypromellose, polyvinyl alcohol (PVA), polyethylene glycol (PEG), dextran, acetylcysteine; sodium chloride; diluents; conventional ointment bases such as oily or greasy bases or water-miscible bases; pH adjusters or buffers; and the like. Advantageously, a surfactant or wetting agent may be included in the composition to facilitate uniform distribution of the compound, for example, on an intraocular lens such as a polymethylmethacrylate device.

Suitable emulsifying agents are those which are inert with respect to the intraocular lens and include dimethyl sulphoxide (DMSO) and surfactants, preferably non-ionic surfactants such as Triton X100 (Trademark), and alcohols such as methanol. Alcohols are not favoured for silicone lenses, and the preferred emulsifier is DMSO. Preferably, the compound is emulsified at a concentration in the range of from about 1–200 $\mu$mol, preferably 2–200 $\mu$mol per litre of 0.1–0.01% DMSO by volume in a balanced salt solution having similar osmolarity to the aqueous humour of the eye, such as Hartmann's solution.

The compositions will usually be accompanied by written or printed directions for use in the medical treatment concerned. The precise dosage used in the treatment by formulations of this invention will depend on the actual calcium intracellular store inactivator (such as a compound of the formula (I)) used, and also on other factors such as the seriousness of the disorder being treated. Formulations adapted for topical ocular administration may contain about 0.1% to 15% by weight of medicament, especially about 0.1 to 2% by weight of medicament, the remainder being comprised of carriers and other excipients well known in the art. Treatment may be by topical ocular administration of about 0.01 to 25 mg and especially 0.2 to 10 mg of compound of formula (I) per day, either by single dose on a 2 to 4 dose per day regimen. The medicament in the topical ocular formulations comprises a calcium intracellular store inactivator (such as a compound of formula (I)) either alone or in combination with a β-adrenergic blocking agent such as timolol maleate or a parasympathomimetic agent such as pilocarpine; or anti-infectives or anti-inflammatories such as a corticosteroid may be included. In such combinations the two active agents are present in approximately equal amounts.

Conveniently, the pharmaceutical compositions according to this invention will be provided in a pack comprising the composition together with a pack insert containing instructions for the use thereof. Preferably, the pack will comprise:
(a) a composition comprising a calcium intracellular store inactivator as described hereinbefore together with an emulsifying agent and/or surfactant; and
(b) instructions for coating an IOL with the composition ex vivo or in vivo.

More preferably, the composition component (a) will itself be in the form of (i) an injectable composition supplied in a sterile syringe for injection into the eye, or (ii) a sprayable composition supplied in a spray container for spraying and thereby coating an IOL.

The pack itself may further comprise (c) an IOL. Very conveniently, pack components (a) and (c) may be contained in a single container having a breakable seal between compartments containing each component.

The present invention therefore provides a calcium intracellular store inactivator such as a compound of formula (I), including thapsigargin and 8-debutanoylthapsigargin per se, or another Ca-ATP-ase inhibitor such as cyclopiazonic acid or an $IP_3$ channel blocker such as caffeine for the preparation or manufacture of a medicament, especially those suitable for ocular use. Preparation of such medicaments or pharmaceutical formulations may be carried out by methods known to those skilled in the art such as by bringing the calcium intracellular store inactivator into intimate physical contact with the pharmaceutically acceptable carrier; for example, by dissolving it therein, or forming a suspension or emulsion therewith. Preferably the composition comprises an intraocular lens coated with the compound by immersing the lens in an emulsion of the compound with a suitable emulsifying agent such as those described above. The IOL to be coated is immersed in the emulsion for around 30 minutes to 1 hour to effect coating. Alternatively, coating may be effected by injecting the emulsion behind the lens in situ.

The present invention therefore further provides an intraocular lens having a coating thereon which coating comprises a calcium intracellular store inactivator, preferably an inhibitor of calcium ATP-ase as defined hereinabove, in particular a compound of formula (I). The coated lens may then be inserted into the eye in vivo or into a capsular bag in vitro.

Compounds of formula (I) other than thapsigargin per se may be prepared by methods analogous to those known to those skilled in the art from thapsigargin or derivatives or analogues thereof. For example, salts of thapsigargin may be prepared by reaction of thapsigargin with suitable bases such as alkali or alkaline earth metal salts of mineral acids; organic acid salts such as the maleate may be prepared by reaction with the corresponding organic acid such as maleic acid. Esters may be prepared by reaction with the corresponding acids. Prodrugs, sometimes known as bioprecursors, comprise derivatives which, when administered to a. living organism, are metabolised into the compound of formula (I) or its salts or esters. Thapsigargin rer se, cyclopiazonic acid and caffeine are each available from Sigma Chemicals; its 8-debutanoyl ester is available from Alexis Corporation (UK) Ltd.

The present invention will now be illustrated by the following examples, with reference to the figures.

EXAMPLE 1

Test Method

Figure 1B:
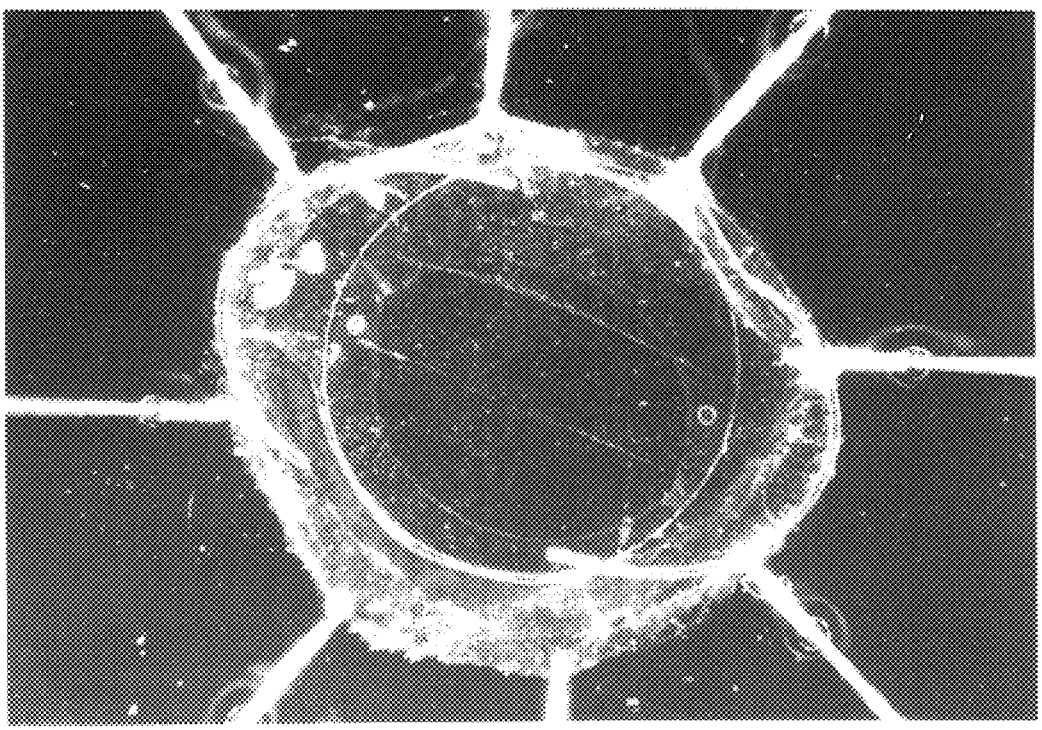

A disc of lens capsule and epithelial cells is removed by a continuous curvilinear tear (capsulorhexis), the lens nucleus is expressed by injection of Hartmann's solution between the remaining capsule and the nucleus (hydroexpression) and the residual soft lens matter is removed with a coaxial irrigation/aspiration cannula (Simcoe's cannula). The capsular bag is dissected free from suspensory ligaments and is then pinned flat on a plastic culture dish (FIG. 1(a)). A coated or uncoated IOL can then be inserted into the bag (FIG. 1(b)) and the preparation is then covered with tissue culture medium (EMEM). Full sterile conditions are maintained throughout. Incubation is at 35° C. with a 5% carbon dioxide ($CO_2$) atmosphere. It has been found that, where the IOL is uncoated and in the presence of 20% foetal calf serum, the posterior capsule becomes covered with epithelial cells in approximately seven days. In the absence of foetal calf serum, the posterior capsule becomes covered with epithelial cells in approximately seven to twenty-five days, depending upon the age of the donor.

Results with Thapsigargin-coated lenses

A human intraocular lens (IOL) coated with thapsigargin may be prepared by preparing 1 μmolar solution of thapsigargin in DMSO and immersing the IOL therein for about one hour; then washing off excess compound by immersion in sterile saline for about one hour.

When serum-free medium was used, no cells grew on the posterior capsule; also cells died on the anterior capsule.

EXAMPLE 2

Following the method of Example 1, 19 PMMA plastic thapsigargin-coated IOLs were inserted into human capsular bags. The bags were cultured in medium (EMEM) without added serum for, on average, 100 days. From the results given in Table 1 (where "died" indicates total cell death), it can be seen that the preferred coating concentration in this test was 2 μM where eventually all cells died and there was no lens epithelial cell growth. When foetal calf serum was present (1–10%), using 2 μM thapsigargin, there was a protective effect with 10 and 5%, but at 1% there was total cell death. The protein concentration of human aqueous humour surrounding the lens is much less than 1% (Dernouchamps in Doc. Ophthalmol. 53 193–248 (1982)).

TABLE 1

Human capsular bags

| Thapsigargin concentration | Lens epithelial cells | |
|---|---|---|
| | Without serum | With serum |
| 200 nM | 4/4 survived | — |
| 2 μM | 7/7 died | 10% 1/1 survived |
| | | 5% 1/1 restricted growth |
| | | 1% 1/1 died |
| 20 μM | 5/5 died | — |

TABLE 2

The effects of thapsigargin on lens cell growth

| Observations | Control | Treatment | | |
|---|---|---|---|---|
| | | 200 nM | 2 μM | 20 μM |
| Total cell cover of posterior capsule | Y | N | N | N |
| Partial cover of posterior capsule | Y | Y | N | N |
| Cell growth on anterior IOL surface | Y | N | N | N |
| Total cell death | N | N | Y | Y |

Figure 2:
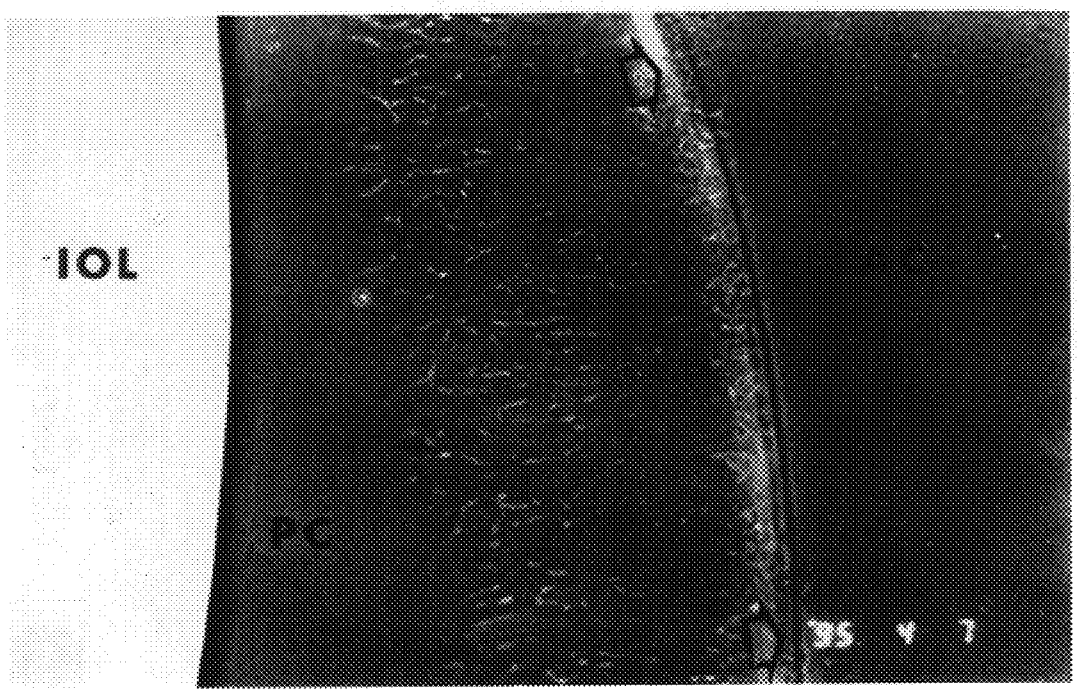
Figure 3:
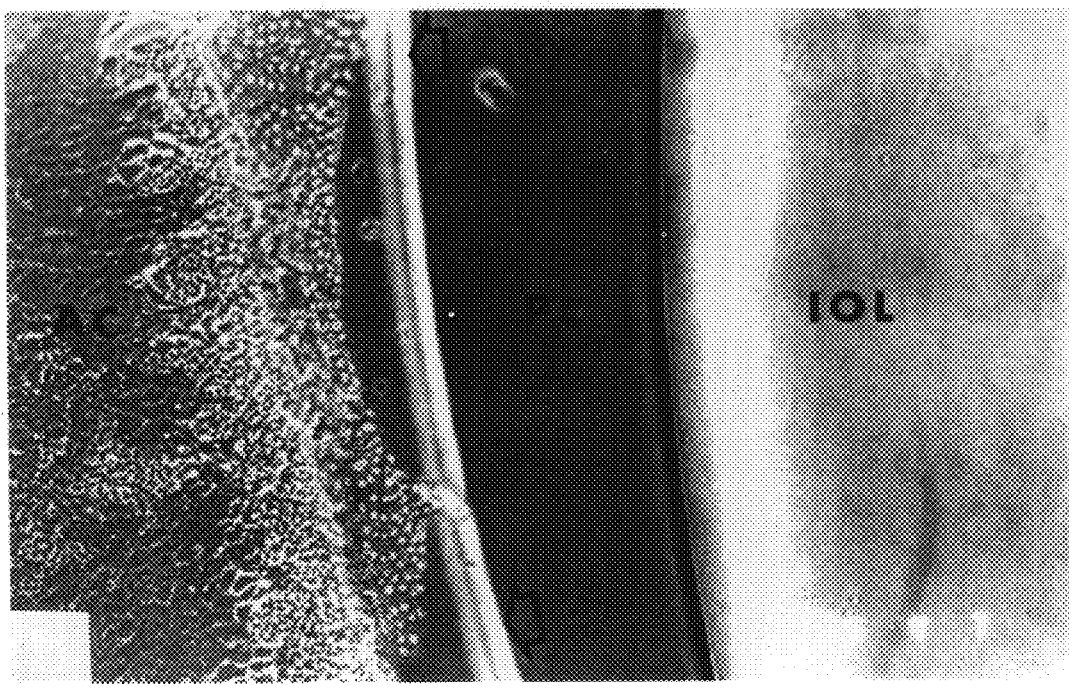

FIGS. 2 & 3 are photographs of phase micrographs of (FIG. 2) cells growing (right to left) on the posterior capsule between the capsulorhexis (arrows) and the edge of the IOL (arrowheads), and (FIG. 3) an absence of growth in the presence of a thapsigargin (20 μM) coated IOL. Both capsules were from the same donor (aged 17 years) and cultured in serum free medium.

EXAMPLE 3

A similar test to that given in Example 2 was carried out on five IOLs but on rabbit capsular bags, cultured without serum. From the results shown in Table 3 can be seen that rabbit tissue is less sensitive than human tissue, requiring in this test a 20 μM concentration of thapsigargin.

TABLE 3

Rabbit capsular bags

| Thapsigargin concentration | Lens epithelial cells without serum |
|---|---|
| 2 μM | 2/2 survived |
| 20 μM | 3/3 died |

EXAMPLE 4

Instead of coating plastic lenses with a calcium ATP-ase inhibitor as in Examples 1 to 3, but simply adding the inhibitor directly to serum-free culture medium (2 human capsular bags each), total lens epithelial cell death in both cases was obtained with 200nanoM thapsigargin and 100 μM cyclopiazonic acid, respectively. These relative potencies of thapsigargin and cyclopiazonic acid on lens epithelial cell growth agree with their relative potencies in causing $Ca^{2+}$ release from the endoplasmic reticulum (Du et al in J. Physiol. London 475P 33–34P (1994)).

EXAMPLE 5

Caffeine (an inositol trisphosphate ($IP_3$) channel blocker) was found to cause total lens epithelial cell growth arrest when added to serum-free culture medium comprising rabbit lens epithelial cells at 5 mM.

EXAMPLE 6

The test method of Example 1, using serum-free medium, was repeated, but using silicon IOLs instead of plastic IOLs. It was found that thapsigargin coated at 2 μM resulted in no lens epithelial cell growth on the lens posterior capsule or IOL.

What is claimed is:

1. A method for inhibiting the growth of lens epithelial cells comprising contacting the cells with a calcium intercellular store inactivator which is an inhibitor of calcium ATP-ase present in the endoplasmic or sarcoplasmic reticulum and which is inert with respect to plasma membrane calcium ATP-ase.

2. A pharmaceutical composition for ocular use comprising: (A) a calcium intracellular store activator which an inhibitor of calcium ATP-ase present in the endoplasmic or sarcoplasmie reticulum and which is inert with respect to plasma membrane calcium ATP-ase and which is a compound of formula (I); and (B) a pharmaceutically acceptable carrier therefor.

3. A composition according to claim 2, comprising eye drops, lotions, solid water-soluble polymeric inserts, gels or ointments, or an intraocular lens or an injection suitable for coating thereon.

4. A compound that is a calcium intracellular store activator which is an inhibitor of calcium ATP-ase present in the endoplasmic or sarcoplasmic reticulum and which is inert with respect to plasma membrane calcium ATP-ase and of formula (I):

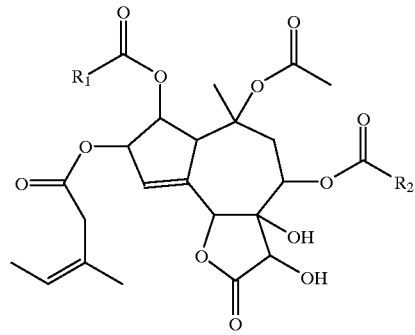

wherein $R_1$ and $R_2$ are each independently straight chain alkyl having from about 3 to 10 carbon atoms or a salt, ester or prodrug thereof other than thapsigargin or 8-debutanoylthapsigargin.

5. An inactivator according to claim 4 wherein $R_1$ is at least heptylene ($C_7H_{15}$) and $R_2$ is at least propylene ($C_3H_7$).

6. The method according to claim 1 wherein the calcium intracellular store inactivator is lipophilic or hydrophobic and exhibits antimigratory, antiproliferative or cytotoxic characteristics with respect to lens epithelial cells.

7. The method according to claim 1 wherein the calcium intracellular store inactivator is thapsigargin.

8. The method according to claim 1 wherein the calcium intracellular store inactivator is selected from thapsigargin and drivatives thereof of the formula:

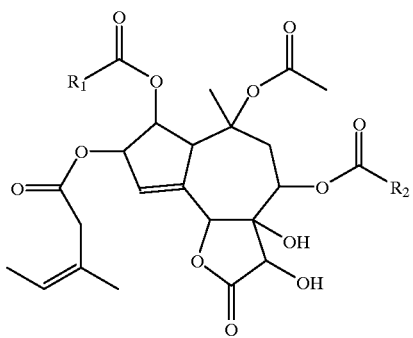

or a salt, ester or prodrug thereof, wherein $R_1$ and $R_2$ are straight chain alkyl.

9. A method for treating after-cataract, glaucoma or surface fouling in a patient comprising administering to the patient calcium intracellular store inactivator which is an inhibitor of calcium ATP-ase present in the endoplasmic or sarcoplasmic reticulum and which is inert with respect to plasma membrane calcium ATP-ase.

10. The method according to claim 1 in which the cells are contacted with an intraocular lens having thereon a coating of said inactivator.

11. A composition according to claim 2 suitable for coating an intraocular lens.

12. A composition according to claim 1 comprising said calcium intracellular store inactivator and an emulsifying agent.

13. A composition according to claim 2 wherein the carrier comprises dimethyl sulfoxide.

14. A method for preventing or inhibiting intraocular lens cell growth comprising bringing the tissue requiring cell growth inhibition into association with a calcium intracellular store inactivator which is an inhibitor of calcium ATP-ase present in the endoplasmic or sarcoplasmic reticulum and which is inert with respect to plasma membrane calcium ATP-ase.

15. A method according to claim 14 wherein the tissue is a lens capsule.

16. A method according to claim 14 wherein the inactivator is a compound of formula (I).

17. A method according to claim 14, comprising treatment associated with after-cataract, glaucoma or surface fouling.

18. A method according to claim 14 comprising administration to a patient in need thereof a lens cell growth-inhibiting amount of thapsigargin.

* * * * *

UNITED STATES PATENT AND TRADEMARK OFFICE
CERTIFICATE OF CORRECTION

PATENT NO. : 6,255,338 B1
DATED : July 3, 2001
INVENTOR(S) : G. Duncan, M. Wormstone, P. Davies and C. Liu Page 1 of 1

It is certified that error appears in the above-identified patent and that said Letters Patent is hereby corrected as shown below:

<u>Column 8, claim 2,</u>
Line 21, after "which" add -- is --.
Line 23, change "sarcoplasmie" to -- sarcoplasmic --.

<u>Column 8, claim 8,</u>
Line 67, change "drivatives" to -- derivatives --.

<u>Column 9, claim 9,</u>
Line 20, change "intracellular" to -- intercellular --.

Signed and Sealed this

Second Day of April, 2002

Attest:

*Attesting Officer*

JAMES E. ROGAN
*Director of the United States Patent and Trademark Office*